(12) United States Patent
Monighetti et al.

(10) Patent No.: US 10,758,706 B2
(45) Date of Patent: Sep. 1, 2020

(54) CATHETER COMPATIBLE STIFFENING STYLET WITH PACKAGING AND DEVICE HOLD ELEMENTS

(71) Applicant: Boston Scientific Scimed, Inc., Maple Grove, MN (US)

(72) Inventors: Katie A. Monighetti, Maynard, MA (US); Laurence D. Brenner, Boylston, MA (US); Ritesh Dahya, Albuquerque, NM (US); Dermot Harney, Galway (IE); Mark Muckian, Cork City (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 105 days.

(21) Appl. No.: 15/813,459

(22) Filed: Nov. 15, 2017

(65) Prior Publication Data

US 2018/0133433 A1 May 17, 2018

Related U.S. Application Data

(60) Provisional application No. 62/423,080, filed on Nov. 16, 2016.

(51) Int. Cl.
*A61M 25/00* (2006.01)
*A61M 25/01* (2006.01)
*A61M 25/09* (2006.01)

(52) U.S. Cl.
CPC ...... *A61M 25/002* (2013.01); *A61M 25/0102* (2013.01); *A61M 25/09* (2013.01); *A61M 2025/0183* (2013.01)

(58) Field of Classification Search
CPC ............ A61M 25/002; A61M 25/0102; A61M 2025/0183; A61M 25/09
See application file for complete search history.

(56) References Cited

U.S. PATENT DOCUMENTS

| 4,636,200 | A | * | 1/1987 | Vaillancourt | ........... A61J 15/00 600/434 |
| 5,372,592 | A | * | 12/1994 | Gambale | ............... A61M 25/00 604/523 |
| 5,507,300 | A | * | 4/1996 | Mukai | ............. A61M 25/09041 600/585 |
| 2006/0278546 | A1 | * | 12/2006 | State | ................... A61M 25/002 206/364 |
| 2015/0094693 | A1 | * | 4/2015 | Suzuki | ............ A61M 25/09041 604/528 |
| 2016/0074628 | A1 | * | 3/2016 | Smith | .................. H04N 5/2253 604/174 |
| 2019/0262577 | A1 | * | 8/2019 | Anderson | .......... A61B 1/00144 |

* cited by examiner

*Primary Examiner* — Theodore J Stigell

(57) ABSTRACT

The present disclosure provides an integrated medical device that includes a stiffening stylet for portions of a catheter along with attachment features for improved functionality and packaging of the catheter system.

20 Claims, 4 Drawing Sheets

CATHETER COMPATIBLE STIFFENING STYLET WITH PACKAGING AND DEVICE HOLD ELEMENTS

CROSS-REFERENCE TO RELATED APPLICATIONS

The present application claims the benefit of priority under 35 U.S.C § 119 to U.S. Provisional Patent Application Ser. No. 62/423,080, filed on Nov. 16, 2016, which is incorporated by reference in its entirety for all purposes.

FIELD

The present disclosure relates generally to the field of minimally invasive catheter-based procedures. In particular, the present disclosure relates to an integrated medical device comprising a stiffening stylet for enhanced structural support of catheter systems and attachment features for improved functionality and packaging.

BACKGROUND

Catheter systems are available for a variety of minimally invasive procedures which are often performed a significant distance from the point of entry within the patient. The distance at which such catheters must maneuver within and through tortuous body passages requires sufficient steerability and pushability along the length of the catheter while maintaining a small cross-sectional profile. This steerability and pushability is often provided, or supplemented, by incorporating a removable guidewire within the catheter lumen. For example, currently available rapid exchange catheter systems provide fast and efficient guidewire removal and/or medical device exchange without the concerted effort of multiple medical professionals. However, the absence of a guidewire extending the full length of the rapid exchange catheter lumen results in a portion of the catheter lacking sufficient columnar support for reliable navigation within small and/or tortuous body passages. For example, a conventional back-loaded rapid exchange catheter may include an unsupported distal portion of 150 cm or more.

An integrated system may provide structural support for the otherwise unsupported portions of a rapid exchange catheter, and improve the overall functionality and packaging of the catheter system, without affecting the operator's ability to front and back load a guidewire within the catheter lumen.

SUMMARY

The present disclosure, in its various aspects, provides advantages in the field catheter systems, and in particular rapid exchange catheters for an integrated medical device comprising a stiffening stylet for enhanced structural support of rapid exchange catheter systems and attachment features for improved functionality and packaging.

In one aspect, the present disclosure relates to a catheter clip, comprising a first portion that includes first and second securement members; a second portion that includes a third securement member; and an elongate member (e.g., stiffening stylet, etc.) attached to and extending from the first portion. The first securement member may be dimensioned or configured to accept (e.g., engage, secure, etc.) a handle portion of a medical device, including, for example a catheter. The second securement member may be dimensioned or configured to accept (e.g., engage, secure, etc.) a protective packaging tube, including for example, a protective packaging tube that contains or houses catheter tubing. The protective packaging tube may include an outer diameter which is greater than an outer diameter of the handle of the medical device.

In another aspect, the present disclosure relates to a medical device clip, comprising a first portion that includes first and second securement members; a second portion that includes a third securement member; and an elongate member (e.g., stiffening stylet) attached to and extending from the first portion. The first securement member may be dimensioned or configured to form an interference fit with a handle of the medical device, the second securement member may be dimensioned or configured to secure one or more loops of the elongate member, and the third securement member may be configured to form an interference fit with a protective packaging tube of the medical device. The first and second securement members may be open-faced and/or open approximately 90 degrees relative to each other. The first securement member may define an opening and a curved inner wall. The opening of the first securement member may include a first width and the curved inner wall may include a first diameter, wherein the first diameter is greater than the first width. The third securement member may define an opening and a curved inner wall, wherein the opening of the third securement member includes a second width and the curved inner wall includes a second diameter, wherein the second diameter is greater than the second width. The protective packaging tube may include an outer diameter that is greater than an outer diameter of the handle of the medical device. The second securement member may include an arm extending above and along an outer surface of the first portion, and an inner surface of the arm may include a recessed portion configured to secure one or more loops of the elongate member between the inner and outer surfaces. The first and second securement members may be positioned or oriented on opposite sides of the first portion. An end of the arm may define an opening having a third width. A proximal end of the elongate member may be affixed, adhered, embedded within the first portion. The elongate member may be removably disposed within a lumen of the medical device.

In another aspect, the present disclosure relates to a method, comprising disengaging a medical device clip from a protective packaging tube, wherein the medical device clip is attached to the medical device and at least a portion of a medical device is contained within the protective packaging tube; removing the medical device from the protective packaging tube; advancing at least a portion of the medical device into a patient; and removing an elongate attached to the medical device clip member from a lumen of the medical device. One or more loops of the elongate member may be gathered within the securement member of the medical device clip as the elongate member is removed from the lumen of the medical device. The method may further include reinserting the elongate member, or a portion thereof, into the lumen of the medical device.

In yet another embodiment, the present disclosure relates to a kit, comprising a medical device clip attached to a medical device, wherein a handle of a medical device is secured within a first securement member of the medical device clip; a protective tubular packaging containing at least portion of the medical device is secured within a third securement member of the medical device clip; and an elongate member (e.g., stiffening stylet) extending from a portion of the medical device clip into and through a lumen of the medical device.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1:
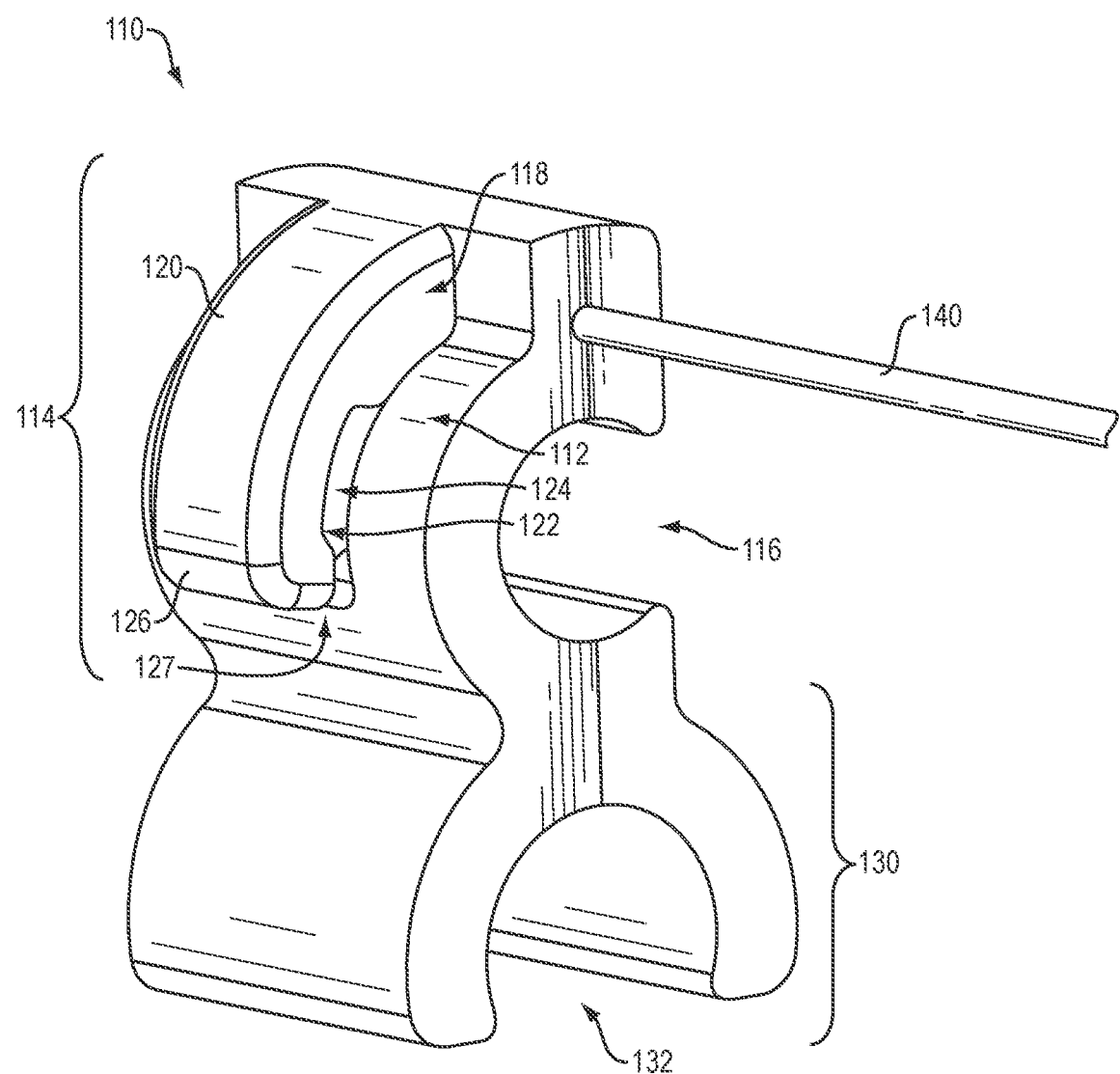
FIG. 1 provides a perspective view of a medical device clip, according to one embodiment of the present disclosure.

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to rapid exchange catheter systems, the medical device clip may be used in a variety of medical systems, including, but not limited to, over the wire catheter systems or any catheter that has an unsupported length of lumen.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

As used herein, "diameter" refers to the distance of a straight line extending between two points and does not necessarily indicate a particular shape.

As used herein, the term "over the wire" (OTW) refers to a catheter system or platform having a guidewire that extends the entire length of the catheter lumen. By way of example, an end of the catheter (e.g., the catheter distal end) may be placed over an end of the guidewire (e.g., the guidewire proximal end), and the catheter advanced over the length of the guidewire until the guidewire exits the opposite end (e.g., the catheter proximal end) at the catheter hub. OTW systems may impart structural support throughout the length of the catheter, thereby imparting "pushability" and/or "steerability" while preventing or limiting unwanted "flexing," "bending" or "kinking" of the catheter during use. However, guidewire removal and/or medical device exchange over the guidewire, requires that the guidewire be removed from the entire length of the catheter. This procedure typically requires the coordinated effort of two or more medical professionals.

As used herein, the term "rapid exchange," "Rx" or "monorail" refers to a catheter system or platform in which only a portion of the catheter lumen is occupied by the guidewire. For example, a rapid exchange catheter may be "front loaded" such that the guidewire only extends through a distal portion (e.g., the last 10-15 cm) of the catheter lumen. Alternatively, a rapid exchange catheter may be "back loaded" such that the guidewire only extends through a proximal portion (e.g., the first 10-15 cm) of the catheter lumen. An advantage of "rapid exchange" catheter systems is that the comparatively small portion of the guidewire extending through the catheter lumen allows guidewire removal and/or device exchange to be performed by a single medical professional. However, the lack of column support along the full length of rapid exchange catheters typically demands that additional structural support be included in the catheter construction, e.g., an integral hypotube, to impart the requisite "pushability." In addition, any medical device or catheter that may be transported or packaged (particularly in a looped or coiled fashion) without an internal support member may be susceptible to damage from kinking or bending.

With reference to an RX catheter as an exemplary embodiment, the present disclosure generally provides a medical device clip which includes a elongate member (e.g., stiffening stylet) configured to improve the stiffness and kink resistance of a rapid exchange catheter without negatively effecting the functionality of the catheter, including, but not limited to, the ability to front load and back load a guidewire. The medical device clip further includes a variety of securement members configured to 1) maintain proper position of the elongate member within the catheter lumen during use, 2) prevent the elongate member from migrating out of protective packaging tube during shipment and storage and 3) collect/store loops of the stylet upon removal from the catheter lumen. Unlike some conventional stiffening stylets the elongate member of the present disclosure is configured to occupy the guidewire lumen without damaging any portion of the rapid exchange catheter, and may be removed to allow a medical professional access to the previously occupied lumen, e.g., to front load a guidewire as necessary during the medical procedure.

Figure 3:
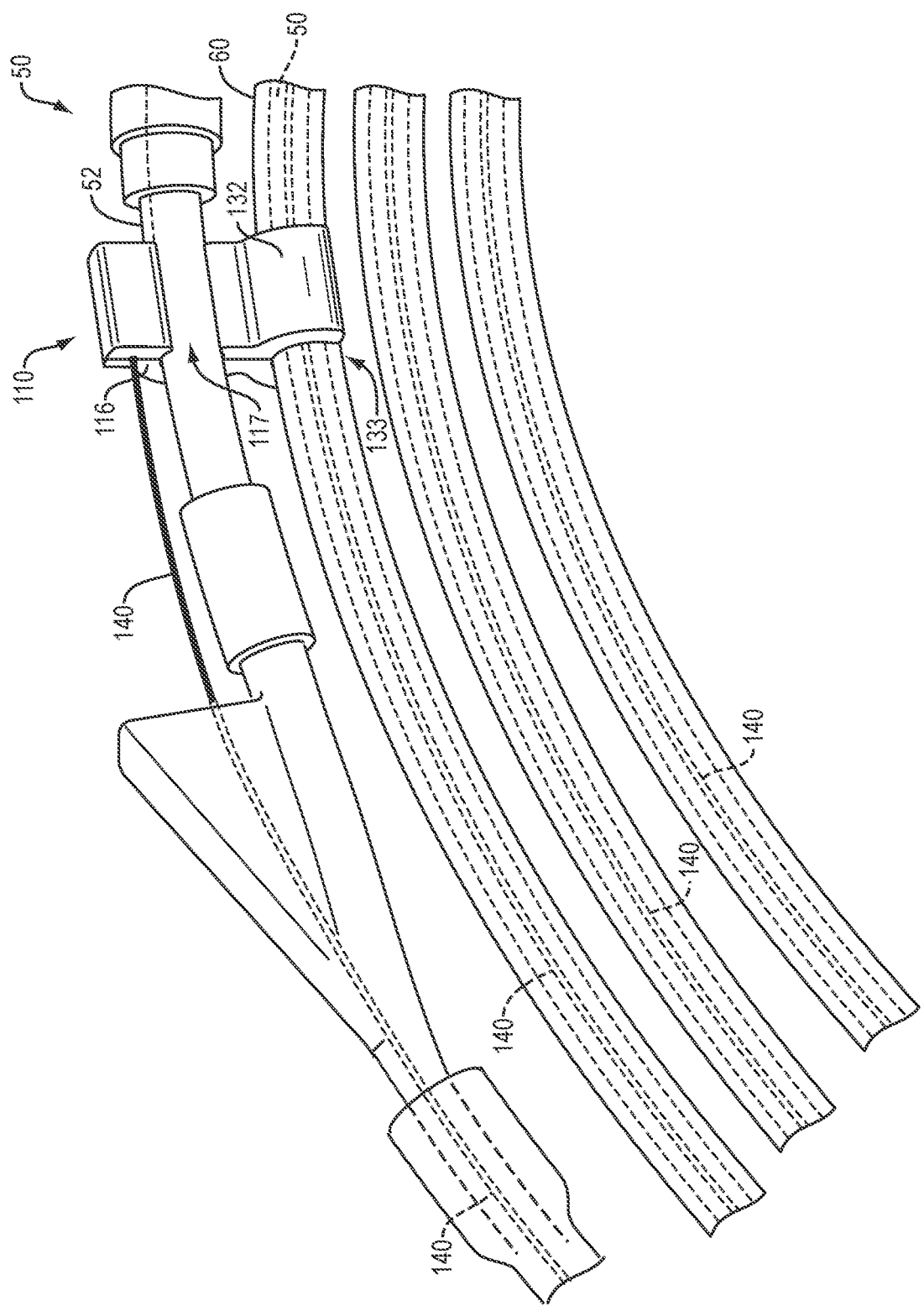
FIG. 3 provides a perspective view of a medical device clip attached to a medical device handle and protective packaging tube, according to another embodiment of the present disclosure.

Referring to FIG. 1, in one embodiment, a medical device clip 110 of the present disclosure may include a first portion 114 comprising first and second securement members 116, 118, a second portion 130 comprising a third securement member 132 and an elongate member 140 attached to and extending outward from the first portion 114. The first securement member 116 may include an open-faced design configured to form an interference fit (e.g., snap fit) with the handle of a medical device (FIG. 3). The open-faced design may further include a rib on either, or both, sides of the opening to enhance the "snap fit" feature. The second securement member 118 may include an arm 120 extending from the first portion 114 towards the second portion 130 along and above an outer surface 112 of the medical device clip 110, on a side of the first portion 114 that is opposite the first securement member 116. The arm 120 may include an end 126 which defines an opening 127 between an inner surface 122 of the arm 120 and the outer surface 112 of the medical device clip. The inner surface 122 of the arm 120 may define a recessed portion 124 configured to secure (e.g., contain, gather, receive etc.) one or more loops of the elongate member. The third securement member 132 may also include an open-faced design configured to form an interference fit (e.g., snap fit) with an outer surface of a protective packaging tube (FIG. 3). The position and/or orientation of the first, second and third securement members about the medical device clip is not limited to the configuration illustrated in FIG. 1. However, in one embodiment, the first and third securement members 116, 132 open approximately 90 degrees relative to each other.

Figure 2:
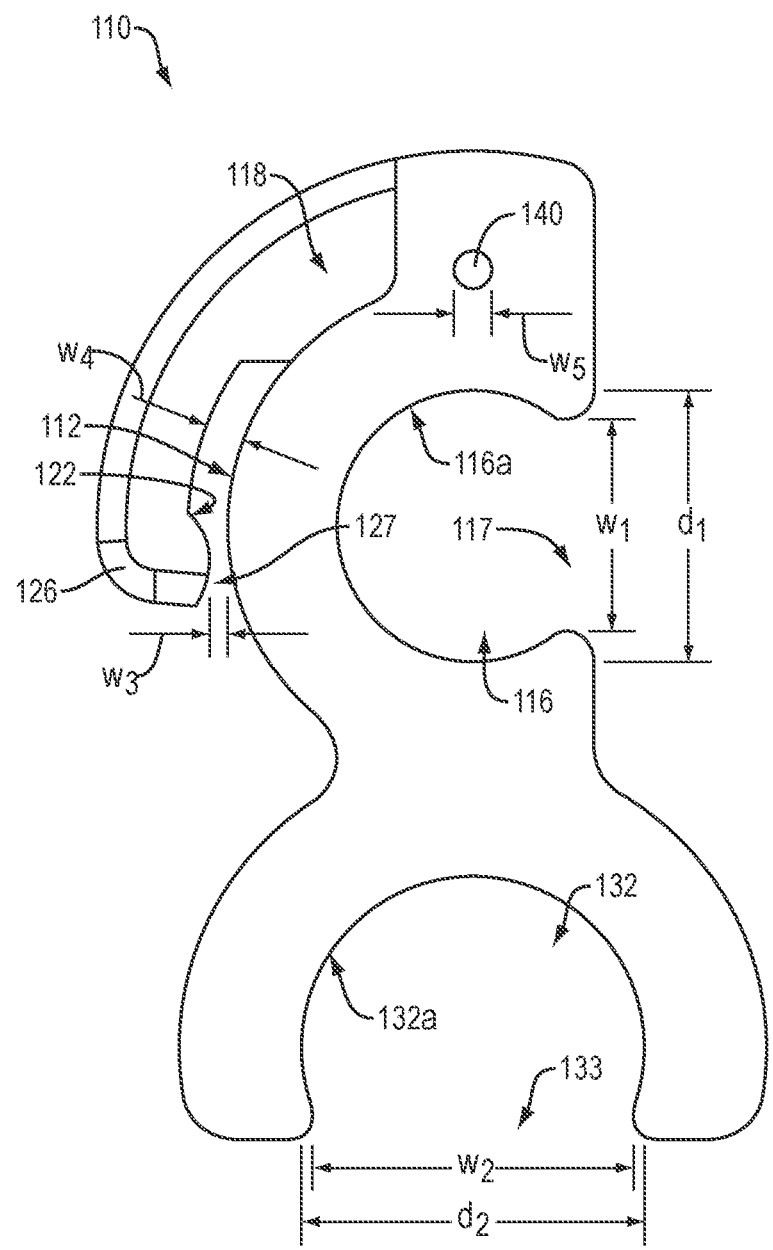
FIG. 2 provides a front dimensional view of a medical device clip, according to one embodiment of the present disclosure.

FIG. 2 provides exemplary dimensions of one embodiment of the medical device clip 110 of the present disclosure. Such dimensions are provided by way of non-limiting example, and are in no way intended to limit the size, shape, arrangement and/or configuration of the medical device clip and/or its components. In one embodiment, the first securement member 116 may define a curved inner wall 116*a* with a first diameter ($d_1$) and an opening 117 with a first width diameter ($w_1$), wherein the first diameter ($d_1$) is greater than the first width ($w_1$). By way of non-limiting example, the first diameter ($d_1$) may be approximately 0.171 inches (e.g., approximately 0.160 inches to approximately 0.180 inches), and the first width ($w_1$) may be approximately 0.133 inches (e.g., approximately 0.120 inches to approximately 0.140 inches). The smaller size of the opening 117 as compared to the diameter of the curved inner wall 116*a* may allow the first securement member 116 to form an interference fit with an outer surface of a medical device handle (e.g., catheter shaft).

The third securement member 132 may define a curved inner wall 132*a* with a second diameter ($d_2$) an opening 133 with a second width ($w_2$), wherein the second diameter ($d_2$) is greater than the second width ($w_2$). By way of non-limiting example, the second diameter ($d_2$) may be approximately 0.214 inches (e.g., approximately 0.200 inches to approximately 0.220 inches), and the second width ($w_2$) may be approximately 0.199 inches (e.g., approximately 0.180 inches to approximately 0.210 inches). The smaller size of opening 133 as compared to the diameter of the curved inner wall 132*a* may allow the third securement member 132 to form an interference fit with an outer surface of a protective packaging tube which contains the medical device (FIG. 3).

The second securement member 118 may define an opening 127 having a third width ($w_3$) of approximately 0.010 inches (e.g., approximately 0.005 inches and 0.020 inches) between the inner surface 122 of the arm 120 and the outer surface 112 of the medical device clip 110. The recessed portion 124 between the inner surface 122 of the arm 120 and the outer surface 112 of the medical device clip 110 may have a fourth width ($w_4$) of approximately 0.025 inches (e.g., approximately 0.015 inches and 0.035 inches). The elongate member 140 may include a cross-sectional width ($w_5$) (e.g., thickness) that is larger than the third width ($w_3$) of opening 127 but smaller than the fourth width ($w_4$) of recessed portion 124. The relatively larger width ($w_5$) of the elongate member 140 as compared to the width ($w_3$) of opening 127 may prevent the loops of the elongate member from disengaging (e.g., falling out of) the second securement member unless acted upon by the medical professional. The unattached end 126 of the arm 120 may impart a degree of flexibility to the second securement member 118, thereby allowing the opening 127 to receive the larger diameter elongate member.

Referring to FIG. 3, the first securement member 116 may be dimensioned to form an interference fit with the handle 52 of a medical device 50 (e.g., catheter etc.), and the third securement member 132 may be dimensioned to form an interference fit with a protective packaging tube 60 which contains the medical device 50. Friction forces between the first and third securement members 116, 132 and the respective portions of the handle 52 and protective packaging tube 60, may be sufficiently low to allow hinged rotation therebetween, but sufficiently high to prevent longitudinal movement (e.g., sliding) along a length of either the handle 52 or protective packaging tube 60. The ability of the medical device clip 110 to prevent, or significantly limit, longitudinal movement may ensure that the elongate member 140 does not migrate within the guidewire lumen of the catheter during shipment or storage, thereby preventing damage to both the elongate member (e.g., bending, kinking etc.) and catheter (e.g., punctures, abrasions etc.). This resistance to longitudinal movement may ensure that the elongate member remains properly positioned within the guidewire lumen while the catheter is being advanced through a body passage. A medical professional may disengage the third securement member 132 from the protective packaging tube 60 using a pivot motion while applying outward pressure (e.g., towards to opening 133) to one or both sides of the protective packaging tube. The protective packaging tube 50 may be re-engaged or locked within the third securement member 132 by applying suitable inward pressure between, e.g., the thumb and forefingers, to snap the protective packaging tube back into the third securement member 132. A medical professional may likewise disengage the first securement member 116 from the handle 52 of the medical device 50 using a pivot motion while applying outward pressure (e.g., towards to opening 117) to one or both sides of the handle. The handle of the medical device may be re-engaged or locked within the first securement member 116 by applying suitable pressure between, e.g., the thumb and forefingers, to snap the handle back into the first securement member 116.

Figure 4:
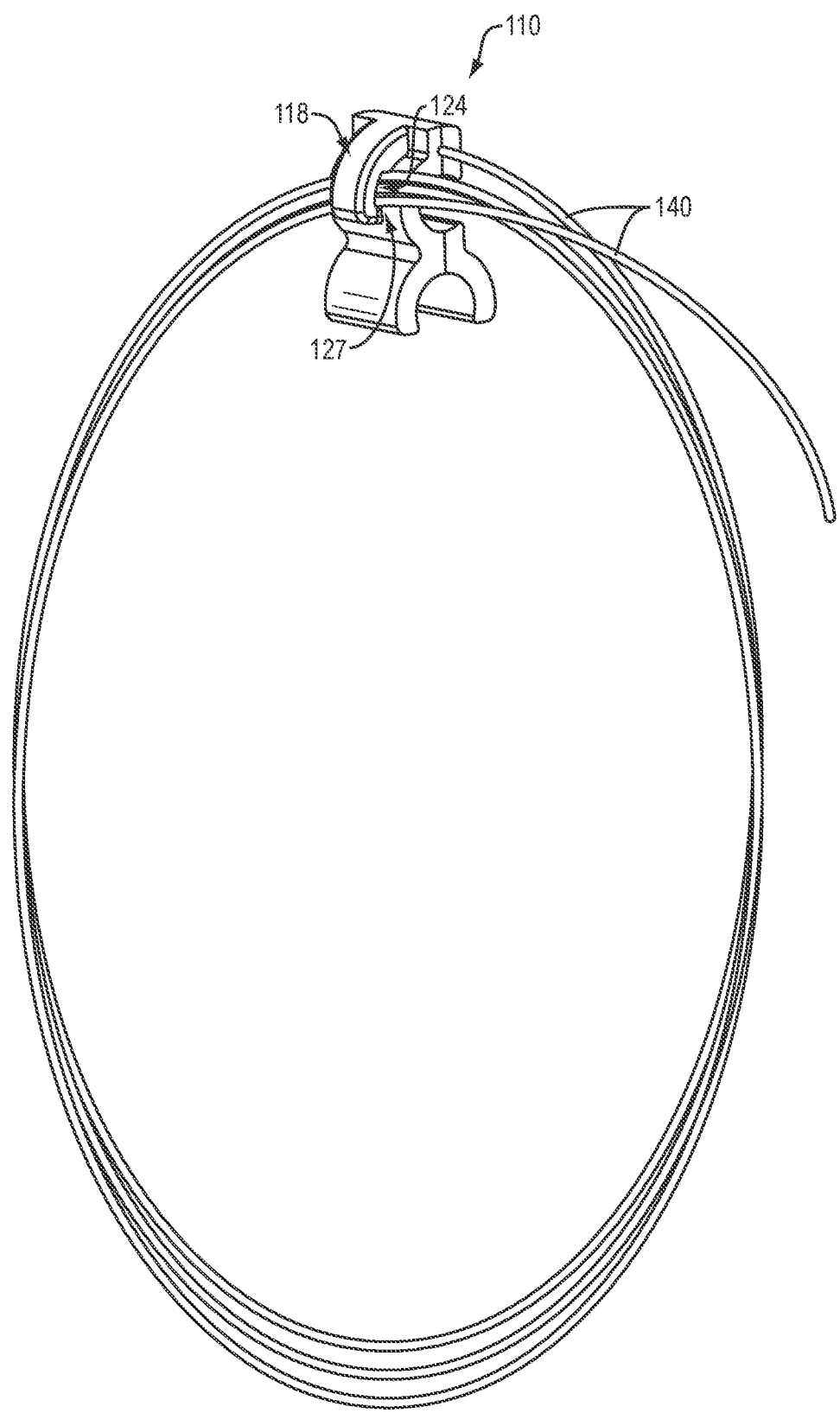
FIG. 4 provides a perspective view of the loops of an elongate member secured within a securement member of the medical device clip, according to another embodiment of the present disclosure.

Referring to FIG. 4, several loops of the elongate member 140 may be secured within the second securement member 118 as the elongate member is removed from the guidewire lumen by applying sufficient force to the advance a section of the elongate member 140 through opening 127 into the larger recessed portion 124. The medical device clip 110 is illustrated independent of the handle and protective packaging tube solely for ease of illustration. An advantage of the medical device clip 110 is the ability to gather, secure and contain one or more loops of the elongate member while the medical device clip remains attached to the handle of the medical device (as illustrated in FIG. 3).

Referring again to FIG. 1, the medical device clip 110 may comprise a variety of suitable polymers which are over-molded onto, or unitarily formed around, the elongate member 140. Examples of suitable thermoplastics may include polyolefins; polyamides (e.g., nylon, such as nylon 12, nylon 11, nylon 6/12, nylon 6, nylon 66); polyesters (e.g., polyethylene terephthalate (PET), polybutylene terephthalate (PBT), polyethylene naphthalate (PEN), polytrimethylene terephthalate (PTT)); polyethers; polyurethanes; polyvinyls; polyacrylics; fluoropolymers; copolymers and block copolymers thereof, such as block copolymers of polyether and polyamide (e.g., PEBAX®); and mixtures thereof. Thus, the elongate member 140 is integrally formed (e.g., embedded within) the material which forms the medical device clip 110. Alternatively, the elongate member 140 may be attached to the medical device clip 110 by a suitable adhesive, glue or resin after the molding process has been performed. For example, a channel or hole may be bored into a surface of the medical device clip and the elongate member 140 inserted into the channel and permanently bonded or affixed. The elongate member may include a variety of lengths (e.g., approximately 75 cm or more; approximately 100 cm or more; approximately 150 cm or more; approximately 300 cm or more) depending on the requirements of the medical procedure. The elongate member 140 may be formed from a variety of sufficiently rigid and flexible materials, including for example, stainless steel. The elongate member 140 may include a thickness that is amenable to insertion into, and withdrawal from, the guidewire lumen of a rapid exchange catheter without damaging (e.g., puncturing, abrading, tearing or otherwise altering) the guidewire lumen. For example, the elongate member may include an outer diameter of approximately 0.020 inches to approximately 0.030 inches. In addition, or alternatively, the elongate member may include a variable thickness along its length such that the distal-most portion of the elongate member is thinner than the more proximal portions (e.g., tapers from the proximal to distal end).

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A catheter clip for securing a catheter, comprising:
   a first portion comprising first and second securement members;
   a second portion comprising a third securement member; and
   an elongate stiffening stylet for the catheter attached to and extending from the first portion;
   wherein the second securement member includes an arm extending above an outer surface of the first portion;
   wherein the second securement member is configured to secure one or more loops of the elongate stiffening stylet.

2. The catheter clip of claim 1, wherein the first securement member is dimensioned to accept a handle of the catheter.

3. The catheter clip of claim 1, wherein the third securement member is dimensioned to accept a protective packaging tube.

4. The catheter clip of claim 1, wherein the first securement member is dimensioned to accept a handle of the catheter and the third securement member is dimensioned to accept a protective packaging tube, wherein a diameter of the protective packaging tube is greater than a diameter of the handle of the catheter.

5. The catheter clip of claim 1, wherein an end of the arm defines an opening having a width.

6. A medical device clip, comprising:
   a first portion comprising first and second securement members;
   a second portion comprising a third securement member; and
   an elongate member attached to and extending from the first portion;
   wherein the first securement member is configured to form an interference fit with a handle of a medical device, the second securement member includes an arm extending above an outer surface of the first portion and is configured to secure one or more loops of the elongate member, and the third securement member is configured to form an interference fit with a protective packaging tube of the medical device.

7. The medical device clip of claim 6, wherein the first and second securement members are open-faced.

8. The medical device clip of claim 6, wherein the first securement member and third securement member open approximately 90 degrees relative to each other.

9. The medical device clip of claim 6, wherein the first securement member defines an opening and a curved inner wall.

10. The medical device clip of claim 9, wherein the opening includes a first width and the curved inner wall includes a first diameter, wherein the first diameter is greater than the first width.

11. The medical device clip of claim 6, wherein the third securement member defines an opening and a curved inner wall.

12. The medical device clip of claim 11, wherein the opening of the third securement member includes a second width and the curved inner wall of the third securement member includes a second diameter, wherein the second diameter is greater than the second width.

13. The medical device clip of claim 6, wherein a diameter of the protective packaging tube is greater than a diameter of the handle of the medical device.

14. The medical device clip of claim 6, wherein an inner surface of the arm includes a recessed portion configured to secure one or more loops of the elongate member between the inner and outer surfaces.

15. The medical device clip of claim 6, wherein the first and second securement members are on opposite sides of the first portion.

16. A catheter clip for securing a catheter, comprising:
    a first portion comprising first and second securement members;
    a second portion comprising a third securement member; and
    an elongate stiffening stylet for the catheter attached to and extending from the first portion;
    wherein the second securement member includes an arm extending above an outer surface of the first portion;
    wherein an inner surface of the arm includes a recessed portion configured to secure at least a portion of the elongate stiffening stylet between the inner and outer surfaces.

17. The catheter clip of claim 16, wherein the first securement member is dimensioned to accept a handle of the catheter.

18. The catheter clip of claim 16, wherein the first and second securement members are open-faced.

19. The catheter clip of claim 16, wherein the first securement member and third securement member open approximately 90 degrees relative to each other.

20. The catheter clip of claim 16, wherein the first securement member defines an opening and a curved inner wall.

* * * * *